US009475887B2

(12) United States Patent
De Paoli Ambrosi

(10) Patent No.: US 9,475,887 B2
(45) Date of Patent: Oct. 25, 2016

(54) CARNOSINE HYALURONIC ACID MIXTURES AND THEIR USE

(76) Inventor: Gianfranco De Paoli Ambrosi, Salo (IT)

( * ) Notice: Subject to any disclaimer, the term of this patent is extended or adjusted under 35 U.S.C. 154(b) by 565 days.

(21) Appl. No.: 13/991,833

(22) PCT Filed: Dec. 6, 2011

(86) PCT No.: PCT/IB2011/002946
§ 371 (c)(1),
(2), (4) Date: Jun. 24, 2014

(87) PCT Pub. No.: WO2012/076961
PCT Pub. Date: Jun. 14, 2012

(65) Prior Publication Data
US 2014/0303116 A1    Oct. 9, 2014

(30) Foreign Application Priority Data

Dec. 6, 2010   (IT) .............................. BS2010A0197

(51) Int. Cl.
*A61K 31/728*    (2006.01)
*A61K 31/198*    (2006.01)
*C08B 37/00*    (2006.01)
*C08B 37/08*    (2006.01)
*A61K 8/49*    (2006.01)
*A61K 8/73*    (2006.01)
*A61K 31/4172*    (2006.01)
*A61Q 7/00*    (2006.01)
*A61Q 19/08*    (2006.01)

(52) U.S. Cl.
CPC ......... *C08B 37/0072* (2013.01); *A61K 8/4946* (2013.01); *A61K 8/735* (2013.01); *A61K 31/198* (2013.01); *A61K 31/4172* (2013.01); *A61K 31/728* (2013.01); *A61Q 7/00* (2013.01); *A61Q 19/08* (2013.01); *A61K 2800/91* (2013.01)

(58) Field of Classification Search
None
See application file for complete search history.

(56) References Cited

U.S. PATENT DOCUMENTS

| | | | | |
|---|---|---|---|---|
| 4,736,024 A * | 4/1988 | Della Valle | .......... | A61K 9/0048 536/101 |
| 6,180,601 B1 * | 1/2001 | Jederstrom | .......... | A61K 9/0014 424/443 |
| 2005/0090662 A1 * | 4/2005 | Beavers | ................ | C07H 7/033 536/53 |
| 2009/0258964 A1 * | 10/2009 | Omura | ................... | A61K 8/042 523/105 |

FOREIGN PATENT DOCUMENTS

| | | |
|---|---|---|
| DE | 102007004916 A1 | 7/2008 |
| WO | 2006067608 A1 | 6/2006 |
| WO | 2010056113 A1 | 5/2010 |

OTHER PUBLICATIONS

Wang, A. et al "Use of carnosine as a natural anti-senescence drug . . . " Biochem. (Moscow) (2000) vol. 65, No. 7, pp. 869-871.*
El-Safory, N. et al "Cytotoxic and antioxidant effects of unsaturated hyaluronic acid oligomers" Carbohyd. Polym. (2010) vol. 82, pp. 1116-1123.*
Caplus abstract for WO 2012076961 (2012) Accession No. 2012:847690.*
Caplus abstract for WO 2011014025 (2011) Accession No. 2011:145298.*
Caplus abstract for JP 2003070452 (2003) Accession No. 2003:187848.*
Caplus abstract for WO 2003013617 (2003) Accession No. 2003:133121.*
Database WPI, XP002633186, Thompson Scientific, London, GB; AN 1992-327694, & JP 4 235111, Aug. 24, 1992.
Yagi M. et al.: "Hyaluronan Modulates Proliferation and Migration of Rabbit Fibroblasts Derived From Flexor Tendon Epitenon and Endotenon", The Journal of Hand Surgery, W.B. Saunders, vol. 35, No. 5, May 1, 2010, pp. 791-796.

* cited by examiner

*Primary Examiner* — Leigh C Maier
(74) *Attorney, Agent, or Firm* — Volpe and Koenig, P.C.

(57) ABSTRACT

A novel compound is disclosed, said compound comprising hyaluronic acid, optionally cross-linked, or an oligomer, optionally cross-linked, dimer or monomer thereof, which is salified or at least partially salified with carnosine, wherein the carnosine is in the form of an L- or D-enantiomer or a racemate; a process for producing this compound, its cosmetic and therapeutic use as well as pharmaceutical and cosmetic compositions containing the same are also disclosed.

2 Claims, 5 Drawing Sheets

Ctrl saline = controls treated with saline

GTA = L-carnosine hyaluronate

Ctrl saline = controls treated with saline

GTB = D-carnosine hyaluronate

GTA = L-carnosine hyaluronate

GTB = D-carnosine hyaluronate

CARNOSINE HYALURONIC ACID MIXTURES AND THEIR USE

FIELD OF THE INVENTION

The present invention relates to the technical field of cosmetic and pharmaceutical industry. In particular, the present invention relates to a compound of carnosine and hyaluronic acid or an oligomer, dimer or monomer thereof, to a method for preparing the same, to cosmetic and pharmaceutical compositions containing the same, and to its use in the cosmetic and/or pharmaceutical field.

KNOWN ART

Carnosine is a dipeptide of amino acids beta-alanine and histidine which is especially present in muscle tissue and brain.

Carnosine has been shown to have antioxidant properties, and particularly the ability to remove reactive oxygen species ("ROS") as well as alpha-beta unsaturated aldehydes formed from peroxidation of fatty acids of cell membrane during an oxidative stress.

Moreover, carnosine inhibits glycation and it is able to chelate divalent metal ions. Due to its antioxidant, anti-glycation and metal-chelating properties, it has been proposed to use carnosine as a supplement in anti-ageing treatment.

A number of studies have shown the beneficial effects of N-acetylcarnosine in the prevention and treatment of cataract, and one of these studies has found that carnosine can reduce the opacity of crystalline lens in rats which had been exposed to guanidine in order to induce cataract (Attanasio F., Cataldo S., Fisichella S., et al. (July 2009) "Protective effects of L- and D-carnosine on alpha-crystallin amyloid fibril formation: implications for cataract disease". Biochemistry 48 (27): 6522-31).

Hyaluronic acid is a saccharide polymer which is widespread in connective, epithelial and neuronal tissue, and it constitutes one of the main components of the extracellular matrix of skin, along with proteoglycans and collagen fibres. Hyaluronic acid consists of alternating and repeating units of glucuronic acid and N-acetyl glucosamine forming a long flexible linear chain of high molecular weight.

Hyaluronic acid is found in vitreous humour, synovial liquid, skin, cartilage, tendons, aortic walls and umbilical cord. Hyaluronic acid has hygroscopic, rheological and viscoelastic properties, and this substance is for many functions in the human organism. Hyaluronic acid is now used in various medical fields including arthrology, aesthetic surgery, ear surgery, ophthalmology and tissue engineering.

From Patent Application WO 2010/056113 there is known an ophthalmic composition comprising dexpanthenol, hyaluronic acid and carnosine, which is especially used as a solution for contact lenses and as eye drops for preventing or reducing superficial punctate keratitis.

From Patent Application WO 2006/087392 there are known dermatological compositions useful against alopecia and containing hyaluronic acid oligomers and trichogenic agents, optionally supplemented with antioxidant compounds among which carnosine is mentioned.

Patent Application EP 1,884,231 discloses colloidal compositions for pharmaceutical or cosmetic use which contain particles of hyaluronic acid combined with a surfactant. These compositions, which are used for treating wounds, burns and acne, can also contain collagen- and elastin-enhancer components among which carnosine is mentioned.

On the other hand, no chemical compound containing hyaluronic acid or an oligomer, dimer or monomer thereof which, when salified with carnosine, forms a defined chemical entity, is known.

SUMMARY OF THE INVENTION

According to one aspect thereof, the present invention relates to a novel compound comprising hyaluronic acid, optionally cross-linked, or an oligomer, optionally cross-linked, dimer or monomer thereof, which is salified or at least partially salified with carnosine, wherein the carnosine is in the form of an L- or D-enantiomer or a racemate.

The term "carnosine" is intended to mean L-carnosine, D-carnosine or a racemic mixture thereof.

"Monomer of hyaluronic acid" is intended to mean the disaccharide unit formed by linking glucuronic acid and acetyl glucosamine via a 1-4 beta glucoside bond.

In the dimer of hyaluronic acid, two of the above monomers are linked to each other via a β 1-3 glucoside bond.

In an oligomer (either in free form or cross-linked) of hyaluronic acid, 3 to 16 monomers are linked to each other to form a molecule with a molecular weight of up to ~6,375 Daltons, corresponding to 16 monomer units and therefore to 16 carboxyl groups.

"Hyaluronic acid" is intended to mean a polymer formed by n-monomers, wherein n is between 17 and 12,500, with a corresponding molecular weight of between 6,772 Da and 5,000,000 Da; therefore, the number of carboxyl groups in hyaluronic acid is between ~17 and 12,500.

"Cross-linked polymer or oligomer" is intended to mean any polymer or oligomer of hyaluronic acid in which there are stable intramolecular bonds of a covalent nature in the form of amides and/or ethers.

Therefore, the compound according to the invention can comprise the monomer of hyaluronic acid, the dimer, the oligomers, either in free form or cross-linked, with a molecular weight of between ~1,192.02 Da and ~6,375 Da, and the polymer (or "hyaluronic acid"), either in free form or cross-linked, with a molecular weight of between ~6,772 Da and ~5,000,000 Da.

The average $M_W$ range of hyaluronic acid is selected depending on the use of the compound. For example, useful ranges comprise 5000-10,000 Da, 10,000-100,000 Da, 100,000-200,000 Da, 200,000-400,000 Da; 400,000-1,000,000 Da, 1,000,000-2,000,000 Da; 3,000,000-4,000,000 Da.

When the compound according to the present invention comprises hyaluronic acid or an oligomer thereof and is optionally cross-linked, it is preferably salified with carnosine on a percentage of its carboxyl groups in the range from 0.001% to 100%, and conveniently from 50 to 100%. Particularly preferred compounds according to the present invention are those in which hyaluronic acid or the oligomer, dimer or monomer thereof is completely salified with carnosine.

In the compound according to the invention, the new chemical entity can be obtained by the process of salifying the primary amino group of the carnosine with the carboxyl group of the glucuronic acid unit. Salification can be performed using the number of moles of carnosine required for salifying the carboxyl group of each monomer, or the number of moles of carnosine required for salifying one or two carboxyl groups of the dimer, or the number of moles of carnosine required for salifying from 3 to 16 carboxyl groups of the oligomers, or from 17 to 12,500 carboxyl groups of the polymer of hyaluronic acid.

The compound according to the present invention is prepared using a process which comprises adding hydrochloric acid to an aqueous solution of an alkaline salt of the hyaluronic acid or a monomer, dimer or oligomer thereof with stirring, wherein the hyaluronic acid or its oligomer can be optionally cross-linked, and then adding carnosine and further stirring at 10-40° C. for at least 1 h until a clear solution is obtained which is then lyophilized to afford the desired compound. The above process is preferably performed under an inert atmosphere, for example a nitrogen atmosphere, and preferably at a temperature of 20-25° C.

The method for preparing the carnosine salt with hyaluronic acid or a monomer, dimer or oligomer thereof, wherein the hyaluronic acid and its oligomers can be optionally cross-linked, can be reproducibly implemented regardless of the degree of polymerization of the hyaluronic acid or its oligomers.

According to another aspect thereof, the present invention relates to a compound as described above for therapeutic use. According to a further aspect, the invention relates to the cosmetic use of the compound described above.

The invention also relates to pharmaceutical compositions for topical use comprising the above compound in combination with a pharmaceutically acceptable vehicle, as well as cosmetic compositions containing the above compound in combination with a cosmetically acceptable vehicle.

The pharmaceutical compositions according to the present invention can be in the form of, for example, eye drops, an injectable preparation for intramuscular, subcutaneous or intra-articular use, impregnated gauze pads, an O/W emulsion, a W/O emulsion, a monophase solution, and an alcoholic solution.

The cosmetic compositions according to the present invention can be in the form of, for example, a lotion, O/W emulsion, W/O emulsion, monophase gel, two-phase gel, micellar two-phase gel, or monophase solution. Said compositions can also be suitable for being injected intracutaneously to fill wrinkles and/or to improve the aesthetic properties of skin, thus delaying the effects of chrono-ageing and photo-ageing, and/or to prevent hair loss.

The compound according to the present invention can have varying uses in the therapeutic and cosmetic field. As for the therapeutic uses, it is possible to contemplate its use in dermatology, ophthalmology, orthopaedics, aesthetic surgery, general surgery, pediatrics, geriatrics and gynaecology. As for the use in the aesthetic field, it is possible to envisage its use in skin creams, in injectable, intracutaneous, anti-ageing preparations, as well as in preparations for treatment of hair and other cutaneous appendages.

In particular, it can be used for the cosmetic and therapeutic applications already mentioned above with reference to carnosine and hyaluronic acid, with the result of obtaining unexpected effects, particularly a synergic effect, compared to these compounds used either alone or in combination with each other.

The compound and the compositions according to the invention can be administered using any available and effective release system, including topical application, injection and transcutaneous administration, in unitary dosage formulations containing conventional carriers, adjuvants and vehicles which are both pharmaceutically or cosmetically acceptable and non-toxic.

The injectable sterile preparations can be formulated in accordance with the known art.

The pharmaceutical preparations according to the present invention can be produced by using conventional pharmaceutical techniques such as those described in the various pharmacopoeias or manuals of the field, such as "Remington's Pharmaceutical Sciences Handbook", Mack Publishing, New York, 18th Ed., 1990.

Further features and advantages of the compound according to the present invention will emerge more clearly from the following description of certain preferred embodiments, with particular reference to methods of preparation and possible instructions for use in the pharmaceutical and/or cosmetic and/or aesthetic field, provided by way of an example which is not limiting or exhaustive.

DETAILED DESCRIPTION

EXAMPLE 1

Preparation of L-carnosine hyaluronate (polymer with $M_W$ of ~300 000 Da)

50 g of $H_2O$ and 0.75 g of NaCl were loaded into a 100 ml round-bottomed flask equipped with a magnetic stir bar under a nitrogen atmosphere, and they were stirred for about 1 minute until completely dissolved. Then, 1 g of sodium hyaluronate with an average $M_W$ of 300,000 Da (batch 09083101 from Shandong Freda Biochemicals) was added and stirring was continued for about 1 minute, followed by the addition of 2.6 ml of 1N HCl with further stirring for about 10 minutes at 20° C. Then, 0.584 g of L-carnosine (equivalent to 2.58 mmol or the number of moles required for salifying all the carboxyl groups in the hyaluronic acid) (supplied by Flamma SpA) and 47 ml of $H_2O$ were added and stirring was continued for 1 h at 20° C., until a clear solution was obtained.

Figure 1:
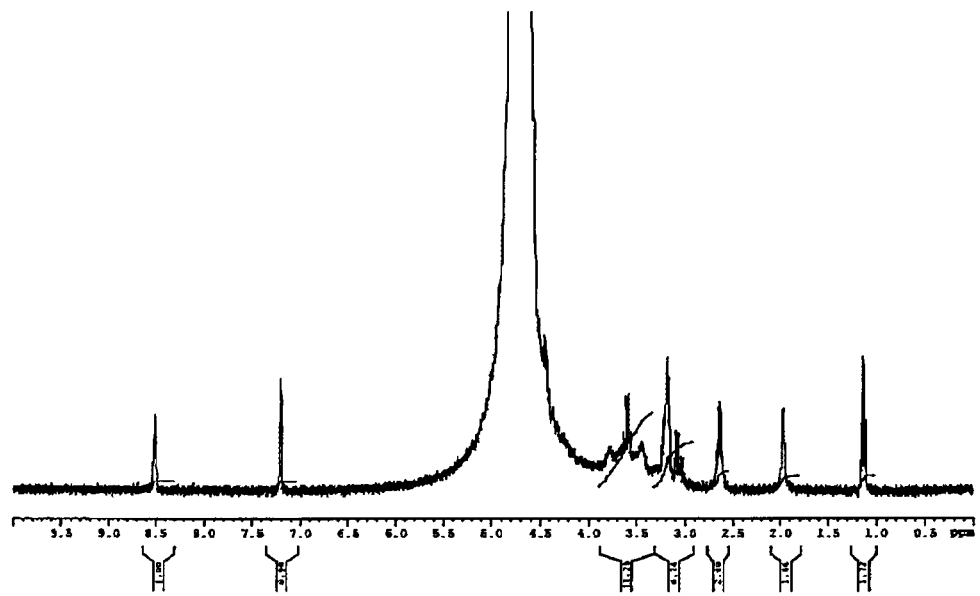
FIG. 1 is an NMR spectrum of L-carnosine hyaluronate in $D_2O$.

1 ml of the final solution was diluted in 5 ml of $D_2O$, and the resulting solution was used to record the NMR spectrum shown in FIG. 1.

Figure 2:
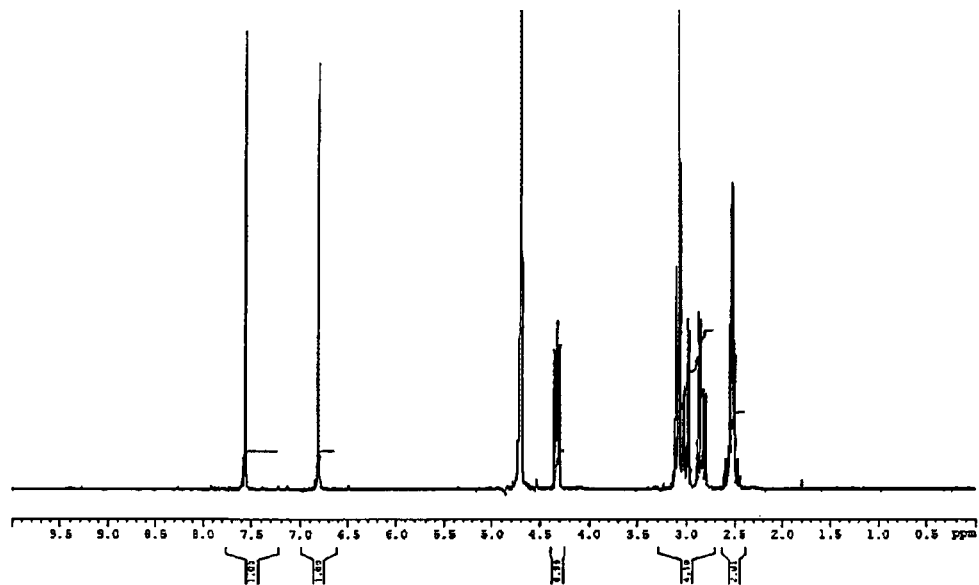
FIG. 2 is an NMR spectrum of L-carnosine in $D_2O$.
Figure 3:
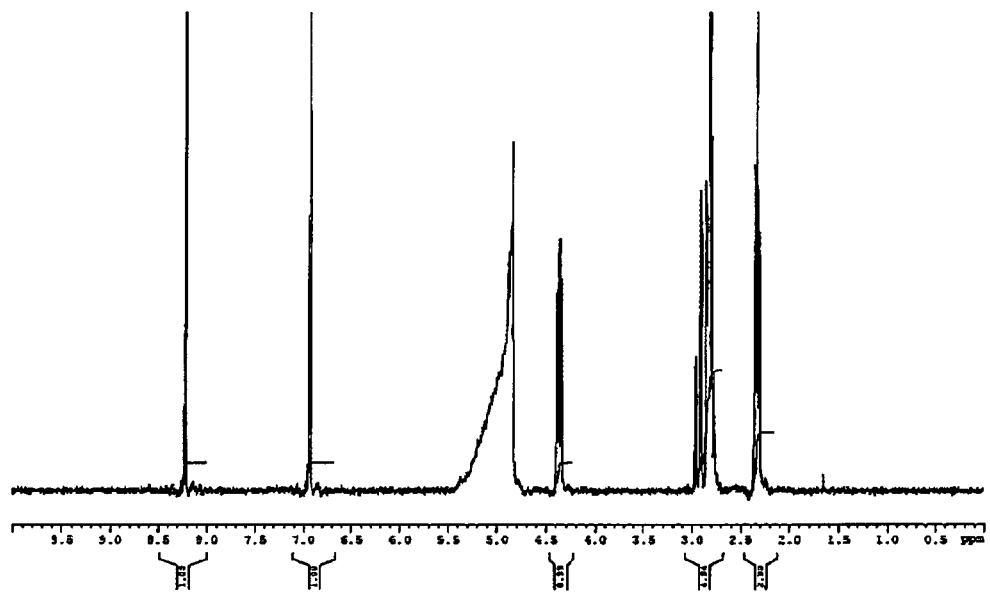
FIG. 3 is an NMR spectrum of L-carnosine in $D_2O+DCl$.
Figure 4:
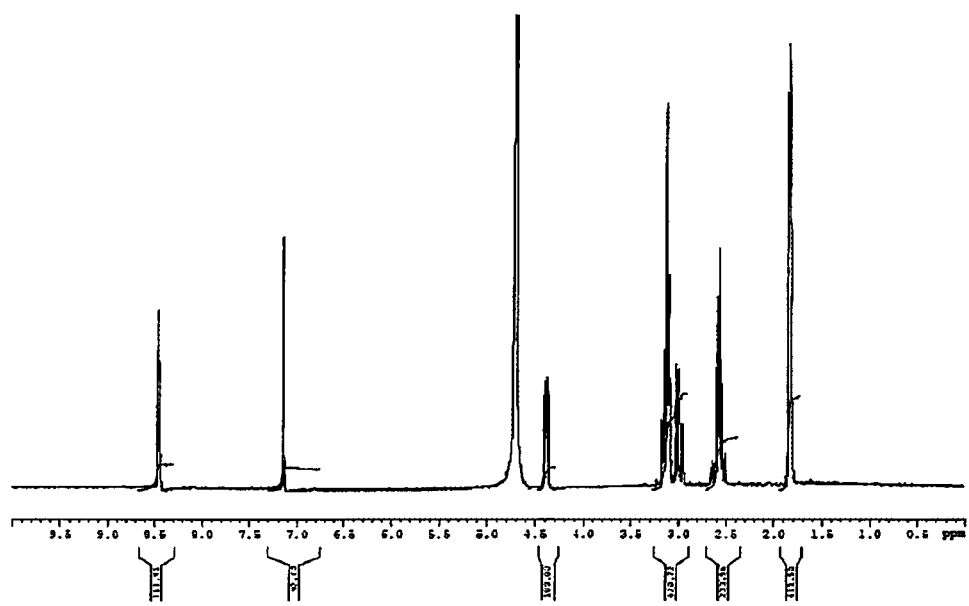
FIG. 4 is an NMR spectrum of L-carnosine in $D_2O$+acetic acid.

For comparative purposes, a solution of L-carnosine in $D_2O$, a solution of L-carnosine in $D_2O$ supplemented with DCl, and a solution of L-carnosine in $D_2O$ supplemented with acetic acid were prepared, and their NMR spectra were recorded as shown in FIGS. 2, 3 and 4, respectively.

The instrument used to obtain the above NMR spectra is a Bruker AV 300 Ultrashield apparatus.

From the spectrum of FIG. 2, it can be noted that carnosine (shown in the formula below)

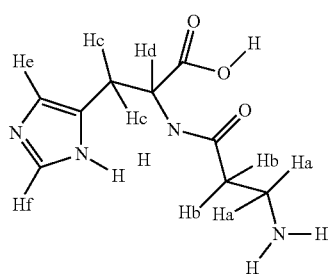

in D₂O has the following signals:

| | |
|---|---|
| 2.5 ppm | m 2H (b) |
| 2.85 ppm | dd 1H (c) |
| 3.00 ppm | dd 1H (c) |
| 3.1 ppm | m 2H (a) |
| 4.3 ppm | m 1H (d) |
| 6.8 ppm | s 1H (e) |
| 7.6 ppm | s 1H (f) |

From FIG. 3, it can be noted that there is a significant change in the chemical shift of signals Ha (from 3.1 to 2.8 ppm) and Hb and in the chemical shift of signal Hf (from 7.6 to 8.2 ppm).

From this it can be assumed that hydrochloric acid salifies both the beta-alanine amino group in L-carnosine and the imidazole nitrogen.

FIG. 4 shows that, when a weak acid such as acetic acid is added, there is also a shift of signals Ha and Hb due to salification of $NH_2$ by acetic acid, even though the amount of this shift is decreased since the strength of acetic acid is comparable to that of the carboxyl group in L-carnosine. A significant shift of signal Hf from 7.6 to 8.5 ppm can also be noted, indicating the salification of the imidazole nitrogen.

FIG. 1 shows that, also in this case, signals Ha and Hb have undergone a shift similar to that recorded for the solution of L-carnosine supplemented with acetic acid, and a significant shift of signal Hf from 7.6 to 8.5 ppm can also be noted. All this confirms that the salt between L-carnosine and hyaluronic acid has been formed.

The solution of L-carnosine hyaluronate prepared as described above was lyophilized to obtain a white powder.

EXAMPLE 2

The procedure shown in Example 1 was followed but using 3 g of sodium hyaluronate with an average $M_W$ of 300,000 Da (batch 09083101 from Shandong Freda Biochemicals), 1.752 of L-carnosine (Flamma SpA), 7.8 ml of 1N HCl, and a total amount of 92 ml of $H_2O$, also in this case to obtain a clear solution of L-carnosine hyaluronate.

EXAMPLE 3

The preparation according to Example 2 was repeated but using D-carnosine (Flamma SpA) instead of L-carnosine, to obtain a clear solution of D-carnosine hyaluronate.

EXAMPLE 4

The solutions obtained from Examples 2 and 3 were used to prepare dilute solutions of L-carnosine hyaluronate and D-carnosine hyaluronate at concentrations of 0.8%, 1.0%, 1.2% and 1.5%, and these solutions, whose pH initially changed from 3 to 1.5, were neutralized by the addition of NaOH.

The effect of the above solutions on the migration of skin fibroblasts was tested in vitro by means of a scratch assay. In this test, cells mimic cell migration during an in vivo tissue repair.

The method is based on scratch-wounding a confluent monolayer of cells so that the cells capable of migration are stimulated to cover the artificial gap in an attempt to re-establish new cell-to-cell contacts.

In order to prevent restoration of the monolayer due to proliferation of the culture cells and not to chemokinesis, fibroblasts are pre-treated with mitomycin C which intercalates DNA to prevent duplication thereof.

In this assay, the fibroblasts were scratch-wounded and then treated with the test substances at different concentrations. At 48 hours after treatment, cells were photographed and stained with crystal violet, and the migrated cells were counted under an optical microscope. The migrated cell count was performed in three fields in three different experiments.

Figure 5:
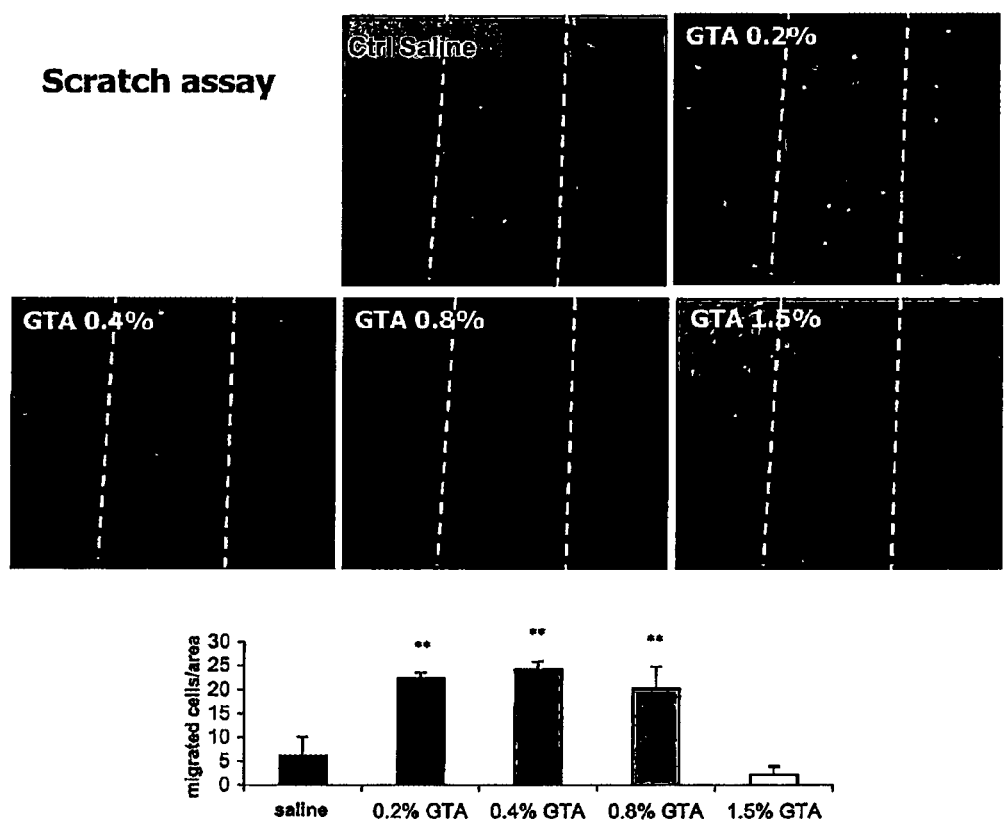
FIG. 5 shows the results of a scratch assay on skin fibroblasts as performed using the compound L-carnosine hyaluronate according to the invention.

FIG. 5 shows a number of photomicrographs and a graphical representation of the scratch assay for the skin fibroblasts. Cells were cultivated in DMEM with 10% FCS and treated with the dilute solutions of L-carnosine hyaluronate as described above for 48 hours after scratching. Morphological analysis was performed under an inverted optical microscope. Cells were counted after staining with crystal violet.

After 48 hours of treatment with L-carnosine hyaluronate, skin fibroblasts can be seen to statistically significantly migrate at low doses of between 0.2 and 0.8%.

Figure 6:
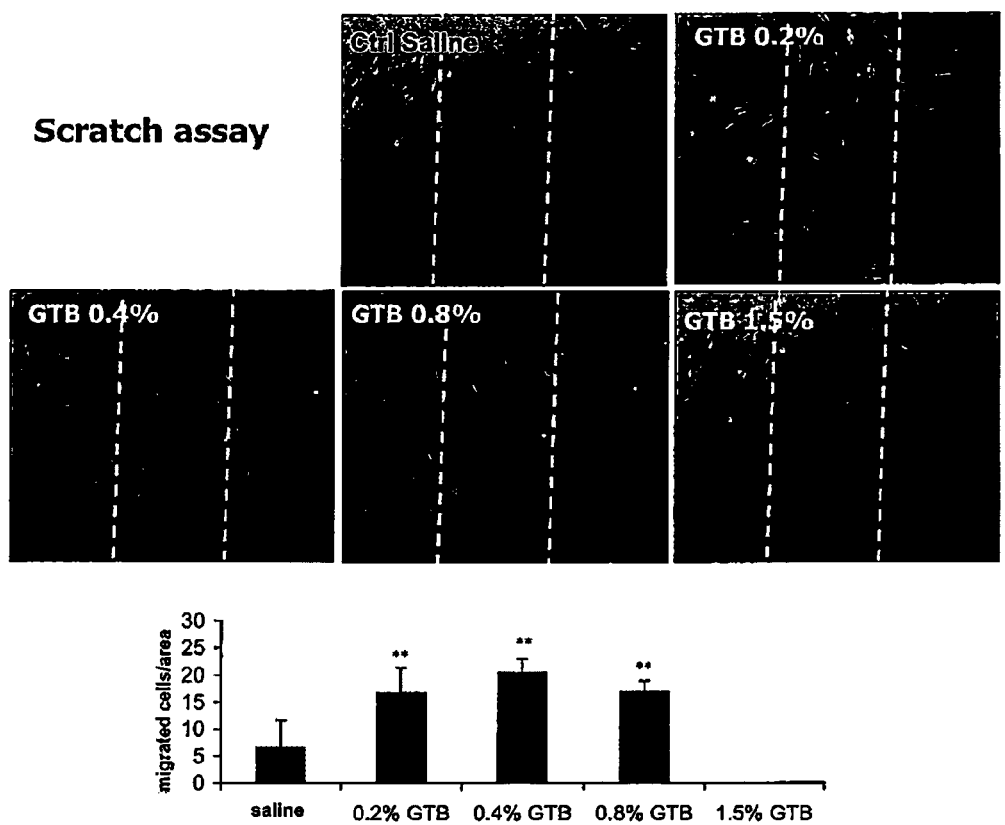
FIG. 6 shows the results of a scratch assay on skin fibroblasts as performed using the compound D-carnosine hyaluronate according to the invention.

FIG. 6 shows a number of photomicrographs and a graphical representation of the scratch assay for the skin fibroblasts. Cells were cultivated in DMEM with 10% FCS and treated with the dilute solutions of D-carnosine hyaluronate as described above for 48 hours after scratching. Morphological analysis was performed under an inverted optical microscope. Cells were counted after staining with crystal violet.

After 48 hours of treatment with D-carnosine hyaluronate, skin fibroblasts can be seen to statistically significantly migrate at low doses of between 0.2 and 0.8%, as in the case of L-carnosine hyaluronate.

EXAMPLE 5

The effect of solutions diluted to 1% and 1.5% and neutralized according to Example 4 on the production of collagen by fibroblasts treated with these solutions was verified.

The Western blotting technique was used to verify any production of collagen by the fibroblasts treated with L- and D-carnosine hyaluronate for 48 hours.

Fibroblast cultures were lysed with RIPA buffer at pH 7.4. Then, the samples were run onto a 10% SDS-polyacrylamide gel under reducing conditions. When the run has been completed, the proteins were transferred onto nitrocellulose membranes, incubated with anti-collagen III antibodies and then with the secondary antibody. The reaction was observed in chemiluminescence. The beta-actin expression was used as an internal control.

Figure 7:
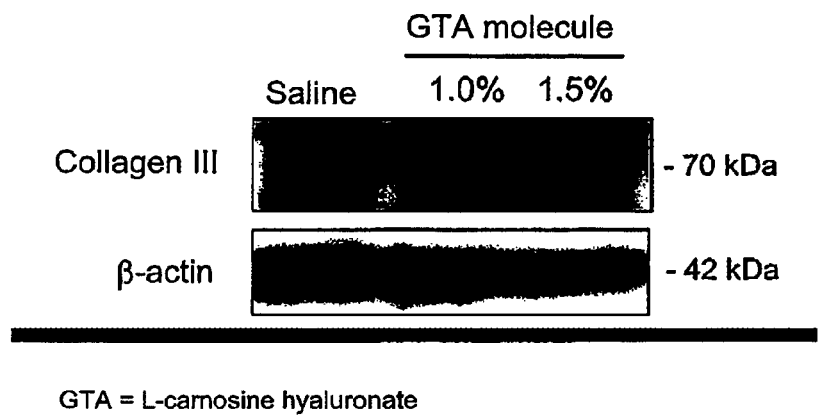
FIG. 7 shows the expression of collagen III in fibroblasts after being exposed to 1.0 and 1.5% L-carnosine hyaluronate for 48 hours, using the Western blotting technique.

As can be noted from FIG. 7, fibroblasts exposed to 1.0 and 1.5% L-carnosine hyaluronate for 48 hours have been shown to synthesize more collagen III than control cells treated with saline.

Figure 8:
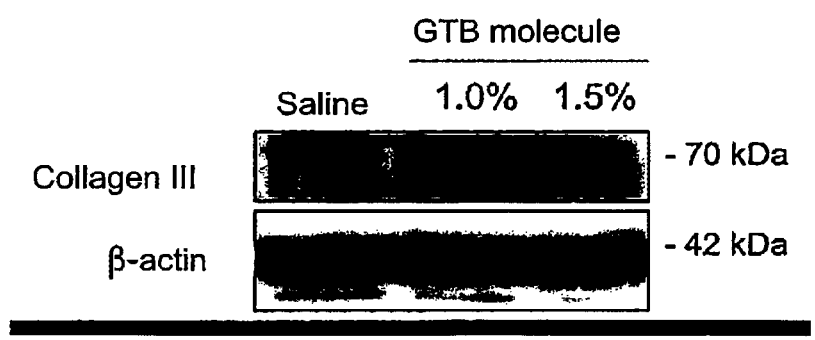
FIG. 8 shows the expression of collagen III in fibroblasts after being exposed to 1.0 and 1.5% D-carnosine hyaluronate for 48 hours, using the Western blotting technique.

From FIG. 8 it can also be noted that fibroblasts exposed to 1.0 and 1.5% D-carnosine hyaluronate for 48 hours have been shown to synthesize more collagen III than control cells treated with saline.

From the experimental results as shown above, it can be concluded that the compound according to the invention can be widely used in various therapeutic fields because of its action both on the migration ability of fibroblasts and on the production of collagen III by fibroblasts, and its use can be contemplated in dermatology, ophthalmology, orthopaedics, aesthetic surgery, general surgery, paediatrics, geriatrics and gynaecology. As for the use of the compound according to the invention in the cosmetic and/or aesthetic field, it is possible to envisage its use in skin creams and in preparations injectable intracutaneously for anti-ageing purposes, as well as in preparations for treatment of hair and other cutaneous appendages.

EXAMPLE 6

Oil-In-Water Emulsion
Phase A

| | | |
|---|---|---|
| | Steareth 2 | 2.00 g |
| | Steareth 21 | 3.00 g |
| | PPG-15 stearyl ether | 9.00 g |
| | Stearic acid | 1.30 g |
| | Cetyl stearyl alcohol | 1.00 g |

Phase B

| | | |
|---|---|---|
| | Carnosine hyaluronate ($M_W$ 400,000 Da) | 0.15 g |
| | Water | 15 g |

Phase C

| | | |
|---|---|---|
| | Preservatives | q.s. |
| | Water | q.s. to 100 ml |

EXAMPLE 7

Solution for Injectable Preparations

| | |
|---|---|
| Carnosine hyaluronate ($M_W$ 400,000 Da) | 50 mg |
| Water per i.p. | 2 ml |

EXAMPLE 8

Solution for Intra-Articular Injections

| | |
|---|---|
| Carnosine hyaluronate ($M_W$ 300,000 Da) | 100 mg |
| Water per i.p. | 1.90 ml |

EXAMPLE 9

Eye Drops

| | |
|---|---|
| Carnosine hyaluronate ($M_W$ 300,000 Da) | 30 mg |
| Saline | 3.36 ml |

The invention claimed is:

1. A process for preparing hyaluronic acid or an oligomer, dimer or monomer thereof at least partially salified with carnosine, wherein the carnosine is in the form of an L- or D-enantiomer or a racemate, the process comprising adding hydrochloric acid to an aqueous solution of an alkaline salt of hyaluronic acid or a monomer, dimer or oligomer thereof with stirring, and then adding carnosine and further stirring for at least 1 h until a clear solution is obtained which is then lyophilized obtaining a powdered saline compound, wherein said process is performed under an inert atmosphere at a temperature of 20-25° C.

2. The process according to claim 1, wherein the hyaluronic acid or its oligomer includes intramolecular cross-links.

\* \* \* \* \*